US00PP24477P2

(12) United States Plant Patent
Kristensen

(10) Patent No.: US PP24,477 P2
(45) Date of Patent: May 20, 2014

(54) ***OSTEOSPERMUM* PLANT NAMED 'SAKOST8365'**

(50) Latin Name: *Osteospermum hybrida*
Varietal Denomination: SAKOST8365

(71) Applicant: Sakata Ornamentals Europe A/S, Marslev (DK)

(72) Inventor: Niels G. Kristensen, Silkeborg (DK)

(73) Assignee: Sakata Ornamentals Europe A/S, Marslev (DK)

( * ) Notice: Subject to any disclaimer, the term of this patent is extended or adjusted under 35 U.S.C. 154(b) by 0 days.

(21) Appl. No.: 13/986,014

(22) Filed: Mar. 22, 2013

(51) Int. Cl.
*A01H 5/00* (2006.01)

(52) U.S. Cl.
USPC ..... Plt./360

(58) Field of Classification Search
USPC ..... Plt./360
See application file for complete search history.

(56) References Cited

U.S. PATENT DOCUMENTS

PP17,703 P3 * 5/2007 Larsen ..... Plt./360

* cited by examiner

*Primary Examiner* — Anne Grunberg
*Assistant Examiner* — Keith Robinson
(74) *Attorney, Agent, or Firm* — Barbara Campbell; Cochran Freund & Young LLC

(57) ABSTRACT

A new *Osteospermum* plant particularly distinguished by having a primrose-yellow flower color when opening and changing to an apricot-pink flower color over 2 to 4 days as the flower ages and a fairly compact and very well-branching plant growth habit, is disclosed.

1 Drawing Sheet

Genus and species: *Osteospermum hybrida.*
Variety denomination: 'SAKOST8365'.

BACKGROUND OF THE NEW PLANT

The present invention comprises a new and distinct variety of *Osteospermum*, botanically known as *Osteospermum hybrida*, and hereinafter referred to by the variety name 'SAKOST8365'. 'SAKOST8365' originated from a hybridization in Marslev, Denmark of the female commercial *Osteospermum* variety 'SAKOST8202', also commercially known as CAPE DAISY™ 'Softly Pink' (U.S. application Ser. No. 13/134,031) having light pink flowers (young flowers have a pinkish-white flower color) and the male *Osteospermum* proprietary breeding line '207011' (unpatented) having pink flowers and yellow disc florets.

In May 2008, the two *Osteospermum* lines 'SAKOST8202' and '207011' were crossed and seeds were obtained. The seeds were sown and plants were grown in pots for evaluation. In February 2009, a line was selected which had a highly unique primrose-yellow flower color when opening and changes to an apricot-pink flower color over 2 to 4 days as the flower ages. This line also has a fairly compact and very well-branching plant growth habit.

In February 2009, the line was vegetatively propagated by cuttings and re-evaluated in an open field and a greenhouse. The line was given the breeder code number '209142' and the stability of the distinct characteristics of this variety was confirmed.

In June 2009, plants from '209142' were evaluated again in pots and in an open field. Line '209142' was subsequently designated 'SAKOST8365' and was found to reproduce true to type in successive generations of asexual propagation via vegetative cuttings.

SUMMARY

The following are the most outstanding and distinguishing characteristics of this new variety when grown under normal horticultural practices in Salinas, Calif.

1. Primrose-yellow flower color when opening and changes to an apricot-pink flower color over 2 to 4 days as the flower ages; and
2. A fairly compact and very well-branching plant growth habit.

DESCRIPTION OF THE PHOTOGRAPHS

This new *Osteospermum* plant is illustrated by the accompanying photographs which show the plant's overall plant habit including form, foliage, and flowers. The photographs are of a plant grown twelve months from transplant into 8-inch pots from rooted cuttings in Salinas, Calif. under greenhouse conditions in the fall of 2012. The colors shown are as true as can be reasonably obtained by conventional photographic procedures.

DESCRIPTION OF THE NEW VARIETY

Figure 1:
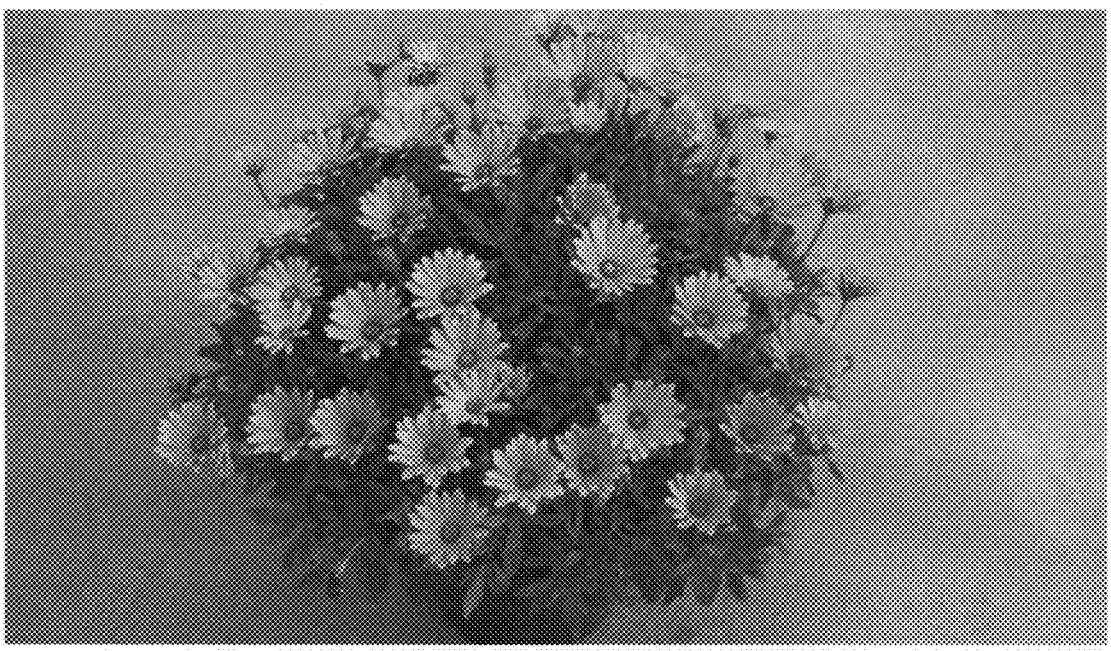
FIG. 1 shows the overall plant habit of the plant grown in a pot.
Figure 2:
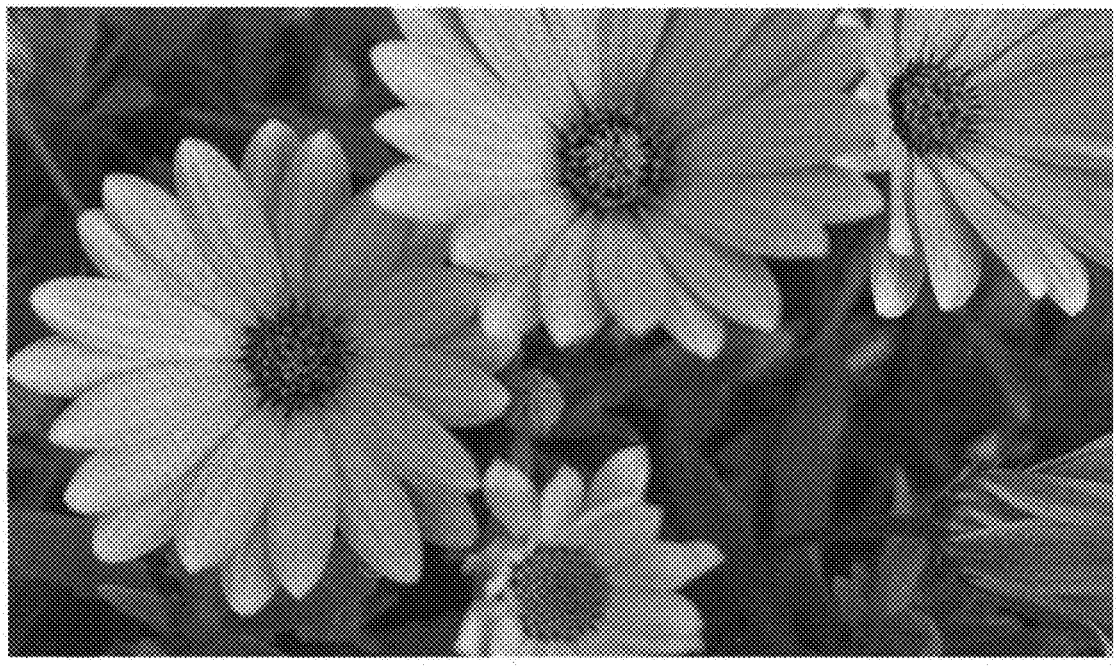
FIG. 2 shows a close-up of the mature inflorescence of the plant.

The following detailed descriptions set forth the distinctive characteristics of 'SAKOST8365'. The data which define these characteristics were collected from asexual reproductions carried out in Salinas, Calif. Data was collected on plants grown approximately twelve months from transplant into 8-inch pots under greenhouse conditions in Salinas, Calif. in the fall of 2012. Color references are to The R.H.S.

Colour Chart of The Royal Horticultural Society of London (R.H.S.), 4th edition. Anatomic labels are from *The Cambridge Illustrated Glossary of Botanical Terms*, by M. Hickey and C. King, Cambridge University.

Classification:

*Family*.—Compositae.

*Botanical*.—*Osteospermum hybrida*.

*Common*.—*Osteospermum*, South African Daisy.

*Designation*.—'SAKOST8365'.

Parentage:

*Female parent*.—The commercial *Osteospermum* variety 'SAKOST8202', also commercially known as CAPE DAISY™ 'Softly Pink' (U.S. application Ser. No. 13/134,031).

*Male parent*.—The proprietary *Osteospermum* line '207011' (unpatented).

Growth:

*Time to produce a rooted cutting*.—Cuttings will colonize a 2.5 cm diameter by 2.5 cm tall greenhouse tray cell with peat-based plant media in approximately four weeks. Cuttings are dipped in a normal dilution (1:9) of Dip 'N Grow root inducing solution in water. The trays are misted hourly during rooting.

*Environmental conditions for plant growth*.—Rooted cuttings are transplanted to pots with a 16 cm diameter, one plant per pot. Peat-based growing media is used. The pots are watered using a 150 ppm to 200 ppm fertilizer solution using 18-8-18 fertilizer. The soil is allowed to dry between watering. During the first few weeks after transplanting, the plants should have evening temperatures around 15° C. to 18° C. for good root growth. When plants reach 7.5 cm to 10 cm in height they are pinched back to 5 to 6 leaves to promote branching. Spring and summer daytime high temperatures in Salinas, Calif. where the data was collected, range from 16° C. to 25° C.

*Time to bloom from propagation*.—Approximately four weeks when rooted vegetative cuttings are transferred to a 5-inch diameter pot. Flowering season is in the spring, summer and fall in the United States. Vernalization is not required to induce flowering.

Plant description:

*Habit*.—Fairly compact and very well-branching.

*Life cycle*.—Perennial.

*Form*.—Semi-erect.

*Height* (*from soil line to first node*).—2.0 cm.

*Height* (*from soil line to top of foliage*).—35.0 cm.

*Width*.—55.0 cm.

Branches:

*General*.—1 main, 6 total; circular in cross-section.

*Length* (*total*).—25.0 cm; approximately 1.0 cm from the soil line to the first node and 3.0 cm between the first and second nodes.

*Diameter*.—0.9 cm.

*Internode length*.—3.0 cm.

*Color*.—RHS 144B (Yellow-Green).

*Pubescence*.—Absent.

*Anthocyanin color*.—Absent.

Stems:

*General*.—Multiple, circular in cross-section.

*Length*.—19.0 cm.

*Diameter*.—0.4 cm.

*Internode length*.—2.0 cm.

*Color*.—RHS 144B (Yellow-Green).

*Pubescence*.—Absent.

*Anthocyanin color*.—Absent.

Leaves:

*Arrangement*.—Alternate.

*Shape*.—Oblanceolate.

*Apex*.—Acute.

*Base*.—Attenuate.

*Margin*.—Serrate.

*Venation*.—Pinnate.

*Surface appearance* (*both surfaces*).—Dull.

*Surface pubescence* (*both surfaces*).—Slight.

*Surface pubescence color* (*both surfaces*).—RHS N155A (White).

*Attachment*.—Decurrant.

*Length*.—6.5 cm.

*Width*.—2.0 cm.

*Thickness*.—Less than 0.1 cm.

*Color*.—Upper surface: RHS 146A (Yellow-Green). Lower surface: RHS 146B (Yellow-Green).

*Venation color* (*both surfaces*).—RHS 146D (Yellow-Green).

Inflorescence:

*Number per plant*.—60 to 70 in bloom.

*Type*.—Capitulum (head); disc florets are perfect and ray florets are carpellate.

*Flowering habit*.—Determinate.

*Lastingness of inflorescence on the plant*.—3 to 4 days.

*Fragrance*.—Absent.

*Seed production*.—None observed.

*Diameter*.—6.5 cm.

*Depth*.—0.5 cm.

*Petal* (*ray floret*) *number*.—21 per inflorescence.

*Disc diameter*.—1.2 cm.

*Disc floret number*.—60 to 80 per inflorescence.

*Peduncle length*.—8.0 cm from inflorescence to first node.

*Peduncle diameter*.—0.2 cm.

*Peduncle color*.—RHS 143A (Green).

*Peduncle texture*.—Dull, slight pubescence.

*Phyllaries*.—Arrangement: 20 per inflorescence, free, arranged symmetrically. Length: 1.0 cm. Width: 0.1 cm. Apex: Acute. Margin: Entire. Shape: Linear; acute. Color (for both upper and lower surfaces): RHS 143A (Green).

Ray florets (ligules):

*Corolla*.—One ray per ray floret; only the outer row of florets are the ray florets.

*Number of ray florets*.—21 per inflorescence.

*Length*.—3.2 cm.

*Width*.—0.7 cm.

*Shape*.—Lanceolate.

*Apex*.—Acute.

*Margin*.—Entire.

*Base*.—Fused.

*Color*.—Upper surface: RHS 18C (Yellow-Orange) with RHS 75A (Purple) stripes and streaks; RHS 75A (Purple) at the base; RHS 10A (Yellow) at the tip Lower surface: RHS 11A (Yellow) with RHS 165A (Greyed-Orange) stripes and streaks.

*Pubescence*.—Glabrous.

Disc florets:

*Color*.—RHS 97C (Violet-Blue).

*Shape*.—Tubular.

*Apex*.—Pointed.

*Texture*.—Dull, pubescent.

*Size*.—Length: 0.6 cm. Width: 0.1 cm.

Reproductive organs:

*Ovary*.—Superior.

*Stigma color*.—RHS N186A (Greyed-Purple).

*Pistil form*.—One style with two stigma branches.

*Pistil length*.—0.7 cm.

*Stamens*.—5, fused into a single tube.

*Style color*.—RHS 155A (White).

*Anther color*.—RHS 165A (Greyed-Orange).

*Pollen color*.—RHS 17A (Yellow-Orange).

*Filament color*.—RHS 155A (White).

Disease and insect resistance: No known resistance or susceptibility.

COMPARISON WITH PARENTAL LINES AND KNOWN VARIETY

'SAKOST8365' is a distinct variety of *Osteospermum* having a primrose-yellow flower color when opening and changing to an apricot-pink flower color over 2 to 4 days as the flower ages and a fairly compact and very well-branching plant growth habit. 'SAKOST8365' is distinguished from its parents as described in Table 1 (color references are to The Royal Horticultural Society Colour Chart, 4$^{th}$ edition).

TABLE 1

Comparison with Parental Lines

| Characteristic | 'SAKOST8365' | Female Parent 'SAKOST8202' | Male Parent '207011' |
|---|---|---|---|
| Ray floret (ligule) color, upper surface | RHS 18C (Yellow-Orange) with RHS 75A (Purple) stripes and streaks; RHS 75A (Purple) at the base and RHS 10A (Yellow) at the tip | RHS 62C (Red-Purple) with young flowers of RHS 155B (White) | Pink |

TABLE 1-continued

Comparison with Parental Lines

| Characteristic | 'SAKOST8365' | Female Parent 'SAKOST8202' | Male Parent '207011' |
|---|---|---|---|
| Disc floret color | RHS 97C (Violet-Blue) | RHS N187A (Greyed-Purple) | Yellow |

'SAKOST8365' is a distinct variety of *Osteospermum* having a primrose-yellow flower color when opening and changing to an apricot-pink flower color over 2 to 4 days as the flower ages and a fairly compact and very well-branching plant growth habit. 'SAKOST8365' is most similar to the *Osteospermum* plant named 'SAKOST3586' (U.S. Plant Pat. No. 20,522). Differences between the two varieties are described in Table 2 (color references are to The Royal Horticultural Society Colour Chart, 4$^{th}$ edition).

TABLE 2

Comparison with Similar Variety

| Characteristic | 'SAKOST8365' | 'SAKOST3586' |
|---|---|---|
| Ray floret (ligule) color, upper surface | RHS 18C (Yellow-Orange) with RHS 75A (Purple) stripes and streaks; RHS 75A (Purple) at the base and RHS 10A (Yellow) at the tip | Yellow-Orange (RHS 18A) at tip and Purple (RHS N78B) at base and streaks of Purple (RHS N78B) from base to tip (fading out closer to tip) |
| Ray floret (ligule) color, lower surface | RHS 11A (Yellow) with RHS 165A (Greyed-Orange) stripes and streaks | Yellow (RHS 12B) with Purple (N77D) streaks mostly at center from base to tip. Petal is White (RHS 155A) at base only. |

I claim:

1. A new and distinct variety of *Osteospermum* plant as shown and described herein.

* * * * *